United States Patent [19]

Roscher et al.

[11] Patent Number: 4,818,347
[45] Date of Patent: Apr. 4, 1989

[54] PROCESS FOR THE ISOLATION OF VINYL ACETATE

[75] Inventors: Günter Roscher, Kelkheim; Karl H. Schmidt, Idstein/Taunus; Hansjörg Hey, Hofheim am Taunus; Horst Langner, Hattersheim am Main; Erwin Andereya, Kelkheim, all of Fed. Rep. of Germany

[73] Assignee: Hoechst Aktiengesellschaft, Frankfurt am Main, Fed. Rep. of Germany

[21] Appl. No.: 133,248

[22] Filed: Dec. 10, 1987

Related U.S. Application Data

[63] Continuation of Ser. No. 53,525, May 19, 1987, abandoned, which is a continuation of Ser. No. 745,410, Jun. 14, 1985, abandoned.

[30] Foreign Application Priority Data

Jun. 18, 1984 [DE] Fed. Rep. of Germany ....... 3422575

[51] Int. Cl.[4] .......................... B01D 3/00; C07C 67/48
[52] U.S. Cl. ......................................... 203/42; 203/78; 203/80; 203/99; 203/DIG. 9; 203/DIG. 10; 203/DIG. 19; 560/248
[58] Field of Search .................. 203/99, DIG. 19, 42, 203/DIG. 10, 71, 73, 78, 80, 14, DIG. 9; 560/248; 202/204

[56] References Cited

U.S. PATENT DOCUMENTS

| | | | |
|---|---|---|---|
| 3,372,187 | 3/1968 | Karnofsky | 560/248 |
| 3,404,177 | 10/1968 | Baba et al. | 560/248 |
| 3,438,870 | 4/1969 | Roscher et al. | 203/14 |
| 3,458,406 | 7/1969 | Fisher et al. | 203/DIG. 10 |
| 3,591,463 | 7/1971 | Copelin | 203/71 |
| 3,692,636 | 9/1972 | Huguet | 203/71 |
| 3,738,915 | 6/1973 | Di Fiore et al. | 203/DIG. 10 |
| 3,838,019 | 9/1974 | Schwerdtel et al. | 560/248 |
| 3,905,875 | 9/1975 | Kronig et al. | 203/14 |
| 4,156,632 | 5/1979 | Roscher et al. | 203/14 |

FOREIGN PATENT DOCUMENTS

| | | | |
|---|---|---|---|
| 0028362 | 5/1981 | European Pat. Off. | 560/248 |
| 2945913 | 6/1981 | Fed. Rep. of Germany | 560/248 |

Primary Examiner—Kenneth M. Schor
Assistant Examiner—V. Mandharan
Attorney, Agent, or Firm—Curtis, Morris & Safford

[57] ABSTRACT

The invention relates to a process for the isolation of vinyl acetate from a gas mixture containing vinyl acetate, ethyl acetate, water and carbon dioxide formed in the reaction of ethylene with acetic acid and oxygen in the gas phase over catalysts containing palladium or palladium compounds. The gas mixture leaving the reaction zone is passed into a distillation column and the gas mixture leaving the top thereof is cooled. The gas which is not condensed during the cooling is washed with acetic acid in a washing column, an acetic acid solution containing vinyl acetate being obtained. The bottom product from the distillation column is passed to a second distillation column and a side stream containing ethyl acetate is removed from an enrichment zone above the bottom thereof, all or some of the bottom product from the second distillation column, which product chiefly consists of acetic acid, being used for the wash in the washing column. The top vapor of the second distillation column is cooled. A portion of the organic phase of the condensate thereby formed is passed, together with the acetic acid solution obtained as the bottom product in the washing column, into a third distillation column, which may have an intermediate tray. The bottom product of the third distillation column is passed into a fourth distillation column. Pure vinyl acetate is removed at the top of the fourth distillation column.

6 Claims, 3 Drawing Sheets

PROCESS FOR THE ISOLATION OF VINYL ACETATE

This application is a continuation, of application Ser. No. 053,525, filed May 19, 1987, now abandoned which is a continuation of Appln. Ser. No. 745,410 filed June 14, 1985, now abandoned.

The preparation of vinyl acetate by reaction of ethylene with acetic acid and oxygen or oxygen-containing gases over fixed bed catalysts in the gas phase is already known. The reaction is in general carried out under pressures of 1 to 25 bar and at temperatures of 100 to 250° C. Suitable catalysts have a noble metal content and an activator content. The noble metal content consists of palladium and/or compounds thereof; gold or compounds thereof can also additionally be present. The activator content consists of compounds of elements of main group 1 and/or main group 2 and/or cadmium. These active components are applied in fine distribution to carriers, silicic acid or aluminum oxide generally being used as the carrier material.

The palladium content in the catalyst is in general between 0.5 and 5% by weight.

If gold or one of its compounds is employed, it is added in an amount of 0.01 to 4% by weight.

In general, each individual activator is also added in an amount of 0.01 to 4% by weight. In the case of all three percentage data, the metal content of the component is in each case based on the total weight of the supported catalyst. The following catalysts are preferred: palladium/alkali metal/cadmium and palladium/gold/alkali metal, it being possible for palladium and/or gold to be in the form of metals or compounds in the finished catalyst and potassium being preferred as the alkali metal element (in the form of a carboxylate).

The catalysts palladium acetate/potassium acetate/cadmium acetate and palladium acetate/barium acetolaurate/potassium acetate are particularly preferred.

On the basis of the stoichiometry, one mole of water is already formed per mole of vinyl acetate:

$CH_2=CH_2+\frac{1}{2} O_2+CH_3COOH \rightarrow CH_2=CHOOC\cdot CH_3+H_2O.$

However, since some of the ethylene reactant burns to give $CO_2$ and water:

$CH_2=CH_2+3 O_2 \rightarrow 2 CO_2+2 H_2O$ more than one mole of water is formed per mole of vinyl acetate; in general, the amount by weight of water formed is about one quarter of the amount of vinyl acetate prepared.

In addition to $CO_2$, smaller amounts of other by-products are formed, and ethyl acetate should be mentioned in particular. Ethyl acetate is formed in an amount of 1,000–2,000 ppm by weight, based on the vinyl acetate formed. However, pure vinyl acetate may in general contain only a maximum of 150 ppm by weight of ethyl acetate. The removal of the ethyl acetate from the vinyl acetate has hitherto required a high expenditure of energy. The invention thus relates to a process with which vinyl acetate can be isolated with a lower consumption of energy, and in particular can be freed from ethyl acetate.

The mixture employed for the reaction contains a several-fold molar excess over the stoichiometry of ethylene. The ethylene conversion in the reaction is accordingly low, and the unreacted ethylene must be recycled to the reaction. Isolation of the vinyl acetate formed from the gas mixture downstream of the vinyl acetate reactor is usually effected in several stages.

In the processes known hitherto, the hot gas mixture which leaves the vinyl acetate reactor and essentially consists of unreacted ethylene, unreacted acetic acid, unreacted oxygen, nitrogen, argon, vinyl acetate, water of reaction, $CO_2$ and ethyl acetate, is passed into a distillation column which operates without additional heating, the so-called preliminary dehydration column (German Offlengungsschrift No. 2,610,624=U.S. Pat. No. 4,156,632). The gas mixture leaving the head of this column is cooled to $-20°$ to $+50°$ C., during which it partly condenses. The condensate separates into two phases, an organic phase and an aqueous phase. The aqueous phase is removed and all or some of the organic phase is recycled as the reflux to the head of the distillation column. The non-condensed portion of the top vapor of this column still contains gaseous vinyl acetate. This is washed out of the gas mixture in a washing column operated with acetic acid as the absorption liquid. The residual gas which remains is recycled to the reactor. A mixture which consists of vinyl acetate, acetic acid, about half the water of reaction and by-products is obtained at the bottom of the distillation column. The other half of the water of reaction has already been removed without supplying energy, and forms the aqueous phase of the condensate formed during the abovementioned cooling of the top vapor of the distillation column. The bottom product of the distillation column and the bottom product of the washing column are combined to give so-called crude vinyl acetate and are distilled together by a known working-up process to give pure vinyl acetate and acetic acid (which is in general recycled to the reaction).

The distillative working up of the crude vinyl acetate is in general carried out by one of the two following processes:

In one of the variants (U.S. Pat. Nos. 3,838,019 and 3,905,875), vinyl acetate and water are distilled over the top of a first column. Acetic acid, which can also contain a little water and in general is recycled to the reaction, is removed as the bottom product. The ethyl acetate, mixed with acetic acid, water and vinyl acetate, is removed from an enrichment zone above the bottom via a lateral take-off. From the distillate of this first column, which separates into two phases, the aqueous phase is removed. Some of the vinyl acetate phase is used as the reflux and thereby simultaneously serves as an azeotrope forming agent for the water to be distilled off over the top. The remainder of the (water-saturated) vinyl acetate phase is dried in a second column by a procedure in which some is distilled over the top as an azeotrope with the water still contained therein, the low-boiling constituents also passing over the top. The anhydrous bottom product of this second column is worked up in a third column to give pure vinyl acetate, which is distilled over the top, and high-boiling constituents and polymers, which are removed as the bottom product.

In the second variant of working up of crude vinyl acetate (U.S. Pat. No. 3,438,870) only two columns are used. In a first column, the water is distilled over the top with vinyl acetate, as an azeotrope-forming agent; from the distillate which separates into two phases, only the aqueous phase is removed and the entire vinyl acetate phase is recycled to the column as a reflux. (In a preferred embodiment, this column contains an intermediate tray. In this case, the reflux of the column is removed from this intermediate tray and passed to a phase separator. The aqueous phase is removed and the vinyl acetate phase is recycled again to the column as a reflux below the intermediate tray. The low-boiling constituents can then be removed directly at the top of the column.) A vinyl acetate/acetic acid mixture which is anhydrous (and if an intermediate tray is used, also free from low-boiling constituents) and which still contains ethyl acetate, high-boiling constituents and polymers is removed as the bottom product of the column and is separated into pure vinyl acetate (top product) and acetic acid containing high-boiling constituents and polymers (bottom product) in a second column. The ethyl acetate is removed from an enrichment zone between the feed and the bottom.

Removal of the ethyl acetate is more advantageous in the 1st distillation variant. In this case, the ethyl acetate enrichment in the first column is effected by the high reflux ratio which is in any case necessary for azeotropic removal of the water. In contrast, in the 2nd distillation variant, a higher reflux ratio than would be necessary merely to separate off the vinyl acetate from the acetic acid must be established for enrichment of ethyl acetate in the second column (the pure vinyl acetate column), and this is unfavorable in terms of energy. On the other hand, the azeotropic removal of the water is more favorable in terms of energy in the 2nd distillation variant, because in this case it takes place in only one column, which is preferably operated under increased pressure (higher conentration of water in the azeotrope). In the 2nd variant, in contrast to the 1st variant, no third column is thus necessary for subsequent drying and for removal of the low-boiling constituents.

It has been found, surprisingly, that the particular advantages of both distillation variants can be utilized in association with the first distillation column, the so-called preliminary dehydration column. The invention thus relates to a process for isolating vinyl acetate from the gas mixture formed in the reaction of ethylene with acetic acid and oxygen in the gas phase over catalysts containing palladium or palladium compounds, in which (a) the gas mixure leaving the reaction zone is passed into a distillation column,
(b) the gas mixture leaving the top of the distillation column is cooled to $-20°$ to $+50°$ C., the condensate obtained forming an aqueous phase and an organic phase,
(c) the aqueous phase formed in step (b) is removed,
(d) all or some of the organic phase formed in step (b) is recycled as a reflux to the top of the distillation column used in step (a), and
(e) the gas not condensed in step (b) is washed in a washing column with acetic acid containing not more than 10% of water, and an acetic acid solution containing vinyl acetate is thereby obtained, which comprises (f) passing the bottom product from step a) to a second distillation column and removing a side stream containing ethyl acetate from an enrichment zone above the bottom thereof,
(g) using all or some of the bottom product from step (f) for the wash in step (e),
(h) cooling the top vapor from step (f), an aqueous phase and an organic phase being formed,
(i) removing the aqueous phase formed in step (h),
(k) recycling some of the organic phase formed in step (h) as a reflux to the top of the distillation column used in step (f),
(l) passing the other portion of the organic phase formed in step (h), together with the acetic acid solution obtained in step e) and if appropriate together with the portion of the organic phase, formed in step (b), which is not used as a reflux in step (d), into a third distillation column,
(m) cooling the top vapor from step (l), an aqueous phase and an organic phase being formed,
(n) removing the aqueous phase formed in step (m),
(o) recycling the organic phase formed in step (m) as a reflux to the distillation column used in step (l),
(p) passing the bottom product from step (l) into a fourth distillation column and
(q) removing the vinyl acetate at the top of the distillation column used in step (p).

However, it is also possible to use a modification of the above process, in which the following two steps are used instead of the above steps (f) and (g) (all other steps remaining unchanged): the bottom product from step (a) is passed to a second distillation column and the bottom product of this column is freed from ethyl acetate by distillation and all or some is then used for the wash in step (e).

In this modification, no side stream containing ethyl acetate is thus removed above the bottom, but the ethyl acetate is in the bottom product and must be separated off from the other components of the bottom product by further distillation.

In step (a), preferably, the gas mixture leaving the reaction zone is first cooled to about 115°–130° C. (during which no condensation of the liquifiable constituents yet occurs) in countercurrent heat exchange with the colder recycle gas (which is thus heated up and then recycled to the reaction), and only then passed into the distillation column.

The amount of organic phase formed in step (b) depends on the cooling temperature chosen in this step. That portion of the oganic phase which is not used as the reflux in step (d) is passed into the third distillation column in step (l) (together with the organic phase from step (h) and acetic acid solution from step (e)). The cooling temperature in step (b) and the portion of the organic phase formed in (b) used as the reflux in step (d) is preferably chosen so that the bottom product of step (a) contains as little vinyl acetate as possible but as far as possible all the ethyl acetate. This means that about 20 to 50% by weight of the vinyl acetate is in the bottom product. The other 50–80% by weight of the vinyl acetate is then 1. in the acetic acid solution formed in step (e) and 2. in the portion of the organic phase formed in step (b) which is not used as the reflux in step (d); both product streams are further processed together in step (l).

The bottom product formed in step (f), which chiefly consists of unreacted acetic acid and contains not more than 10% by weight of water, is in general employed in step (e). A portion of the bottom product mentioned which is not required in step (e) is preferably recycled to the reactor, after a small amount has been discharged to remove high-boiling constituents and polymers.

In step (k), preferably, only an amount of the organic phase formed in step (h) such that the top vapor of the second distillation column is free from acetic acid and ethyl acetate is recycled as the reflux. The portion of the organic phase which is not required for this purpose is passed into the third distillation column, in accordance with step (l). This column is preferably operated under increased pressure, for example under 1.5 to 10 bar.

In a preferred embodiment; the third distillation column just mentioned contains an intermediate tray and steps (m), (n) and (o) are replaced by the following steps $\alpha$, $\beta$ and $\gamma$:

($\alpha$) the top vapor from step (1) is cooled and most of the condensate formed is recycled as a reflux to the top of the distillation column used in step (l), whereas the smaller portion is discharged to remove low-boiling constituents; the entire reflux from the intermediate tray of the column is then removed and is allowed to separate into an aqueous phase and an organic phase, ($\beta$) the aqueous phase formed in step ($\alpha$) is removed and ($\gamma$) the organic phase formed in step ($\alpha$) is recycled again to the third distillation column, below the intermediate tray.

Steps (p) and (q) follow unchanged, but in the case of the preferred use of the intermediate tray, the bottom product removed in step (p) is already free from low-boiling constituents.

Some of the vinyl acetate removed in step (q) is recycled as a reflux to the top of the distillation column used in step (p), but preferably not more than is necessary, so that all the acetic acid remains in the bottom product.

The surprising advantage of the process according to the invention is the energy-saving removal of the ethyl acetate formed in the vinyl acetate reaction, removal of the ethyl acetate from some of the vinyl acetate already takes place in the distillation column (which is used in step (a)). In fact, virtually all of the ethyl acetate remains in the bottom product of the distillation column, whereas the portion of vinyl acetate which is not condensed in step (b), which portion is obtained in step (e) in the form of an acetic acid solution, contains virtually no ethyl acetate, and it is therefore not necessary to free this vinyl acetate part stream from ethyl acetate, which expends energy. In the fourth distillation column (which is used in step (p), a reflux ratio of about 0.6 can be established, because of the absence of ethyl acetate. (In contrast, a reflux ratio of 3 was necessary in the second column of the 2nd distillation variant mentioned above as the prior art, because the ethyl acetate was still present here). Considerably less energy (in general heating steam) is thus required for the fourth distillation column of the present process than for the 2nd column of the known 2nd distillation variant. Furthermore, since in the present process virtually all of the ethyl acetate is removed in step (f) (preferably) or its abovementioned modification (page 7), both of which require a high reflux ratio anyway because of the discharge of water simultaneously carried out (see steps (h) and (i)), virtually only the same expenditure on distillation is necessary for this removal of ethyl acetate as in the 1st column of the abovmentioned 1st distillation variant of the prior art. However, the latter variant additionally requires a 3rd column for subsequent drying of the vinyl acetate, which is not necessary in the present process.

BRIEF DESCRIPTION OF THE DRAWINGS

A particularly preferred embodiment, which consists of steps (a) to (p), $\alpha$, $\beta$, $\gamma$ and p and q, is illustrated by FIG. 1.

Figure 1:
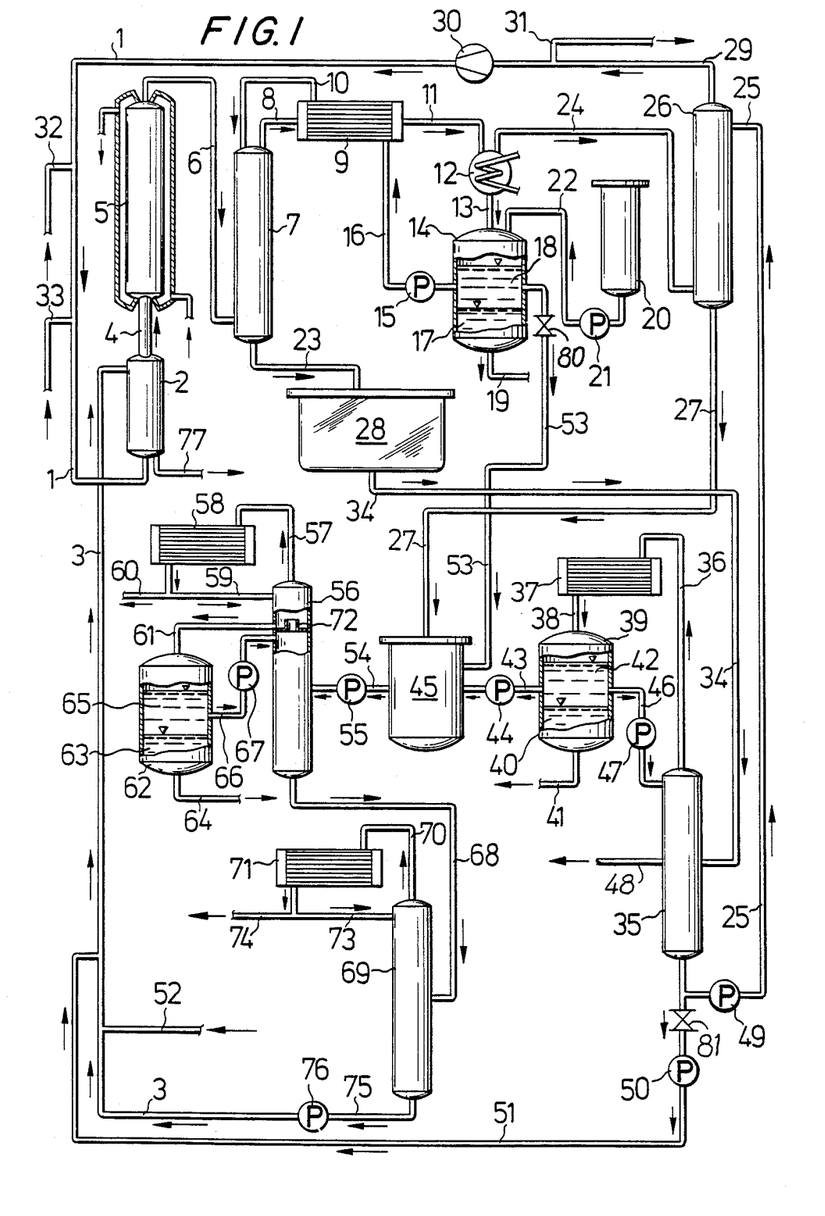

The recycle gas consisting of ethylene, oxygen and $CO_2$ is passed via line (1) into an acetic acid vaporizer (2), designed as a bubble column, in which the stream of gas is charged with acetic acid, which is fed in via line (3). The gas mixture leaving the acetic acid vaporizer (2) is passed via a steam-heated line (4) to the reactor (5). This consists of a reaction tube which is 5.60 m in length, has an internal diameter of 32 mm and is surrounded by a jacket. The heat of reaction is removed by means of boiling water under pressure in this jacket. The reaction tube is filled catalyst material. The gas mixture, which essentially consists of ethylene, acetic acid, vinyl acetate, ethyl acetate, water, carbon dioxide, oxygen and inert substances, such as, for example, nitrogen and argon, leaving the reactor (5) is passed via line (6) into the distillation column (7). Column (7) is 2.5 m long and 50 mm in diameter. It is filled with a packing of rolled VA wire netting (so-called Goodloe packing). The gas mixture leaving column (7) over the top passes via line (8) to a heater exchanger (9), where it is brought into countercurrent heat exchange with the reflux, which enters via line (16) and is recycled via line (10) to column (7). The gas mixture passes from the heat exchanger (9) via line (11) into a water-cooled condenser (12), in which it is cooled to about 35° C. The contents thereby liquefied pass via line (13) into container (14), where they are collected. The portion of liquid which exceeds a certain level in the collection container (14) is pumped back via line (16), heat exchanger (9) and line (10) into the distillation column (7) by means of a pump (15). The condensate obtained in the collection container (14) separates into two phases (17) and (18); the aqueous phase (17) is discharged via line (19) and all or some of the organic phase (18) only is pumped back via line (16), heat exchanger (9) and line (10) as the reflux to the top of the distillation column (7). Stabilizer solution is pumped from the stock vessel (20) via the pump (21) and line (22) into the collection container (14). The liquid which is obtained at the bottom of the distillation column (7) and which chiefly consists of vinyl acetate, acetic acid and water and essentially contains all the ethyl acetate, is removed via line (23) to the container (28). The gas mixture which leaves the condenser (12) via line (24) is freed from the non-condensed portions of vinyl acetate in the washing column (26) charged with acetic acid via line (25); the bottom product from column (26) passes via line (27) into the container (45). The residual gas (ethylene, unreacted oxygen and $CO_2$ formed as a by-product) leaving the washing column (26) via line (29) is recycled via line (1) and the acetic acid vaporizer (2) to the reactor (5) by means of the recycle gas compressor (30). A part stream of the recycle gas is removed via line (31) as waste gas to discharge inert substances. Fresh ethylene is passed in via line (32) and fresh oxygen is passed in via line (33).

The mixture from the container (28) is passed via line (34) into the distillation column (35). The top vapor of column (35) is passed via line (36) into condenser (37) and liquified there. The condensate passing via line (38) into container (39) separates into an aqueous phase (40), which is removed via line (41), and an organic phase (42), some of which is passed via line (43) and pump (44) to the container (45), whereas the other portion is recycled via line (46) and pump (47) as the reflux to the column (35), in order to prevent acetic acid and ethyl acetate discharge to the top product. The ethyl acetate contained in the mixture in container (28) and entering column (35) via line (34) is removed from an enrichment zone above the bottom of the column (35) via line (48). The bottom of column (35) contains acetic acid, not more than 10% by weight of water and small amounts of high-boiling constituents and polymers, and only traces of vinyl acetate and ethyl acetate.

The aqueous acetic acid from the bottom discharge of column (35) is divided. The portion required for the acetic acid wash in step (d) is passed via pump (49) and line (25) into the washing column (26). The remainder is recycled again to the acetic acid vaporizer (2) valve (81), pump (50), line (51) and line (3). Since the amount of acetic acid required as washing liquid varies depending on the design of the washing column (26) and the temperature of the gas to be washed, the division of the stream of acetic acid from the bottom of the column (35) can also vary. Fresh acetic acid is fed into the acetic acid vaporizer (2) via lines (52) and (3) in an amount corresponding to the acetic acid consumed in the reaction. As stated, the bottom discharge of column (26) is passed via line (27) to the container (45), as is some of the organic phase (42) from container (39). Furthermore, the remainder of the organic phase (18) from the collection container (14) passes via valve (80) and line (53) into container (45), if not all the organic phase (18) is used as the reflux in the distillation column (7). The liquid in the container (45) is passed via line (54) and pump (55) to the column (56), which is operated under increased pressure. The top vapor of column (56) is passed via line (57) to the condenser (58); almost all the condensate obtained is recycled via line (59) as the reflux to column (56). A small part stream is discharged via line (60) to remove the low-boiling constituents.

The column (56) contains a intermediate tray (72). From this intermediate tray, all the reflux in this column is removed via line (61) and passed to the phase separation vessel (62). The aqueous phase (63) obtained is removed via line (64). The organic phase (65) is recycled via line (66) and pump (67) to the column (56) below the intermediate tray (72)

The dry vinyl acetate/acetic acid mixture obtained at the bottom of column (56) is passed via line (68) to the column (69). The top vapor of this column passes via line (70) to the condenser (71). The condensate obtained is pure vinyl acetate which is virtually free from ethyl acetate. This vinyl acetate is recycled via line (73) as the reflux to column (69) in an amount such as is necessary to keep the distillate free from acetic acid. Pure acetate is removed via line (74). The bottom product of the column (69), which contains acetic acid, high-boiling constituents and traces of vinyl acetate/ethyl acetate, is recycled via line (75) and pump (76) to line (3) and then into the acetic acid vaporizer (2), from which a part stream is removed via line (77) to discharge polymers.

Figure 2:
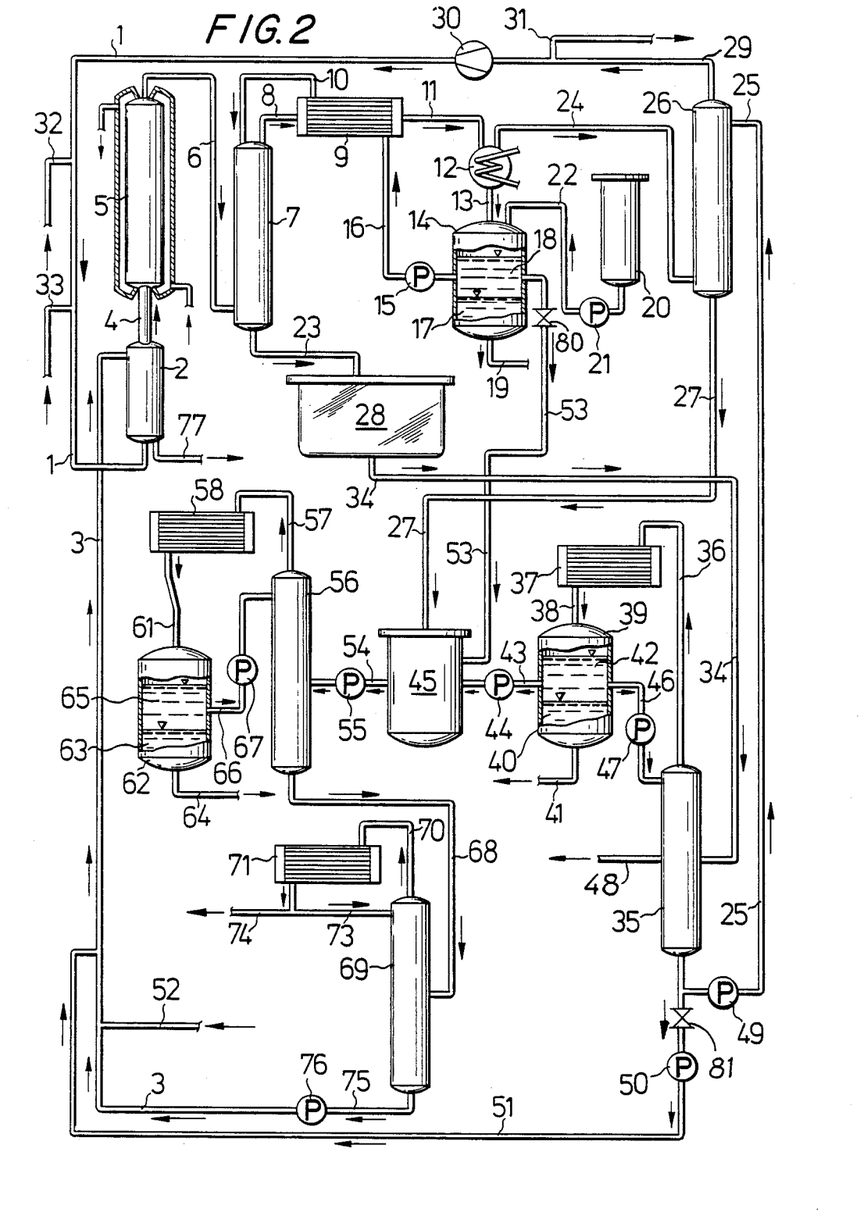

Another embodiment of the present invention, which includes unmodified steps (a) to (q), is illustrated by FIG. 2. In this embodiment, all steps are the same as described in FIG. 1 except column (56) does not contain an intermediate tray (72). The top vapor of column (56) is passed via line (57) to condensor (58). The condensate obtained is removed via line (61) and passed to phase separation vessel (62). The aqueous phase (63) obtained is removed via line (64). The organic phase (65) is recycled via line (66) and pump (67) to column (56). All remaining steps are as described for FIG. 1.

Figure 3:
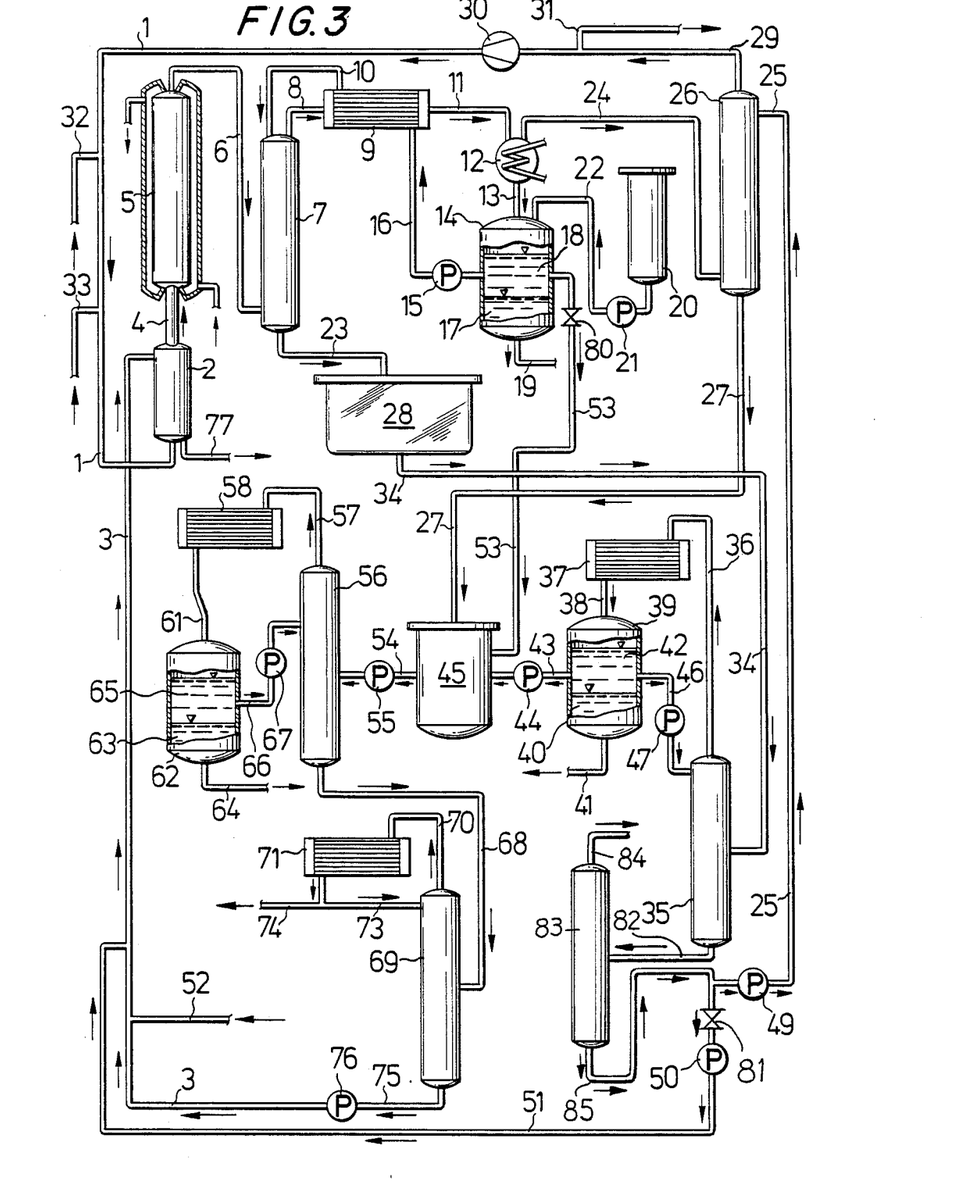

A further embodiment of the present invention which includes modified steps (f) and (g) (see page 7) with otherwise unmodified steps (a) to (q) is illustrated by FIG. 3. In this embodiment, the ethyl acetate contained in the mixture in container (28) and entering column (35) via line (34) is removed from the bottom of column (35) via line (82) together with the aqueous acetic acid discharge from the bottom of column (35). No sidestream containing ethyl acetate is thus removed above the bottom of column (35) via line (48). The bottom discharge of column (35) is passed via line (82) into auxiliary distillation column (83). Ethyl acetate is removed from auxiliary distillation column (83) via line (84). The aqueous acetic acid from the bottom discharge of column (83) passes via line (85) and is divided. The portion required for the acetic acid wash in step d) is passed via pump (49) and line (25) into washing column (26). The remainder is recycled again to acetic acid vaporizer (2) via valve (81), pump (50), line (51) and line (3). Except for removing a sidestream containing ethyl acetate from an enrichment zone above the bottom of column (35) via line (48), all the remaining steps shown in FIG. 3 are the same as in FIG. 2.

EXAMPLE

The following experiment was carried out in the apparatus just described and shown in FIG. 1. The reactor (5) is filled with 4.4 liters of a known vinyl acetate catalyst containing 2.3% by weight of palladium, 2% by weight of potassium and 1.9% by weight of cadmium in the form of their acetates, on silica gel support (beads 4–6 mm in diameter). 12 Nm$^3$ per hour of a mixture containing about 69% by volume of ethylene, 24% by volume of carbon dioxide and 7% by volume of oxygen are passed into the acetic acid vaporizer (2). An amount of acetic acid is passed to the acetic acid vaporizer (2) via line (3) such that 4.83 kg per hour of acetic acid vaporize in the vaporizer. 0.5 kg per hour of material is removed from the acetic acid vaporizer (2) via line (77) to discharge high-boiling constituents and polymers. The reactor inlet gas is preheated to 155° C. in line (4). An increased pressure of 8 bar (9 bar absolute) is established at the inlet of the reactor (5), and the reactor outlet temperature is established at 160° C. via the pressure on the boiling water cooling system in the outer jacket of the reactor. The temperature of the reactor outlet gas at the inlet of the distillate column (7) is only 130° C. (because of the radiation of heat from line (6)). The gaseous mixture leaving the distillation column (7) via the top is cooled to 35° C. in the condenser (12). 9 kg per hour of organic phase (18) are obtained in the container (14) and are recycled via pump (15) and heat exchanger (9) to the distillation column (7). 350 g per hour of aqueous phase (17) containing 3% by weight of vinyl acetate, 0.1% by weight of acetic acid and 0.05% by weight of acetaldehyde are removed from the container (14). At the bottom of the distillation column (7), in which a top temperature of 80° C. and a bottom temperature of 90° C. are established, 4 kg per hour of a mixture of the following composition are obtained: 74% by weight of acetic acid, 7.5% by weight of water, 17.5% by weight of vinyl acetate, 0.05% by weight of ethylidene diacetate, 0.06% by weight of ethyl acetate, 0.1% by weight of acetaldehyde and 0.05% by weight of high-boiling constituents and polymers. 15 ml per hour of a solution of 2.5% by weight of p-benzoquinone in vinyl acetate are pumped from stock vessel (20) into the container (14) for stabilization.

The residual gas from the condenser (12) is passed via line (24) into the washing column (26). 3.1 kg per hour of water-containing acetic acid are pumped from the bottom of the column (35) via line (25) to the top of the washing column (26). 5 kg per hour of a mixture of the following composition are obtained at the bottom of the washing column (26): 57.6% by weight of acetic acid, 5.1% by weight of water, 37% by weight of vinyl acetate, 0.02% by weight of acetaldehyde and 30 ppm by weight of ethyl acetate.

The gas leaving the washing column (26) is recycled via line (29) and the recycle gas compressor (30) to the acetic acid vaporizer (20). Ethylene consumed in the reaction and the oxygen consumed are replaced by passing fresh ethylene—line (32)—and fresh oxygen—line (33)—to the recycle gas. $CO_2$ formed as a by-product in the reaction is removed from the recycle gas as waste gas via line (31); the amount of waste gas is adjusted so that a $CO_2$ concentration of 24% by volume is maintained in the recycle gas.

The bottom discharge of the distillation column (7) is let down via line (23) into the stock vessel (28) and from there is passed via line (34) into the column (35). Column (35) is a glass column with a vacuum jacket, an internal diameter of 50 mm, a length of 6 m and 80 bubble trays, with electrical heating of the bottom.

4 kg per hour of the mixture of container (28) are introduced at the 40th tray of column (35). The heating of the bottom is adjusted so that the total amount of distillate is 3 kg/hour. 100 g/hour of aqueous phase (40) are obtained in the phase separator (39) and are removed. An amount of the organic phase (42) is pumped via line (43) to the container (45) (about 0.7 kg/hour) such that the temperature in column (35) at the 25th tray is 112° C. Most of the organic phase (42) is recycled as the reflux via line (46) into the column (35). The organic phase (42) removed after container (45) still contains, in addition to vinyl acetate: 0.05% by weight of acetic acid, 0.2% by weight of acetaldehyde, 0.015% by weight of ethyl acetate and 1.3% by weight of water.

A lateral take-off (48) is located at the 20th tray of the column (35), from which 50 g per hour of material containing about 5% by weight of ethyl acetate, 2% by weight of vinyl acetate, 12% by weight of water and 81% by weight of acetic acid are removed. The water content of the bottom product acetic acid of column (35) is 6% by weight, the bottom product is passed via line (25) into the washing column (26).

5.7 kg per hour of a product of the following composition are obtained in container (45): 51.1% by weight of acetic acid, 44.1% by weight of vinyl acetate, 4.8% by weight of water, 0.04% by weight of acetaldehyde and 45 ppm of weight of ethyl acetate.

This mixture is further distilled in column (56). this is made of V$_4$A steel and has 80 trays and bottom heating with a steam-heated circulatory evaporator. The feed is located at the 45th tray. An intermediate tray (72) is located above the 60th tray in the column, from which the entire reflux of the column is passed over the phase separator (62). The column is operated under a top pressure of 1 bar gage (2 bar absolute). The bottom heating is adjusted so that 6 kb/hour of organic phase (65) are obtained in the phase separator (62), the organic phase (65) being recycled back to the column (56) below the intermediate tray (72) via line (66). 278 g/hour of aqueous phase (63) are also obtained in the phase separator (62), the aqueous phase (63) being removed. 20 g per hour of condensate are removed at the top of column (56) via line (60), the condensate containing about 50% by weight of vinyl acetate, 47% by weight of acetaldehyde (formed by vinyl acetate hydrolysis) and about 2.5% by weight of water. The bottom discharge of column (56) is further worked up in column (69). The column is made of glass and has electrical heating of the bottom. At a reflux ratio of 0.6, 2.4 kg per hour of vinyl acetate containing less than 50 ppm by weight of acetic acid, about 100 ppm by weight of water and 40 ppm by weight of ethyl acetate are obtained via line (74). The bottom product acetic acid, which still contains 54 ppm by weight of ethyl acetate and 60 ppm by weight of vinyl acetate, is recycled via line (75), pump (76) and line (3) to the acetic acid vaporizer (2) in the reaction section.

We claim:

1. A process for isolating vinyl acetate from a gas mixture containing vinyl acetate, ethyl acetate, acetic acid, water and carbon dioxide formed in the reaction of ethylene with acetic acid and oxygen in a reaction zone in the gas phase over catalysts containing palladium or palladium compounds, which comprises
    (a) passing the gas mixture leaving the reaction zone into a first distillation column,
    (b) cooling the gas mixture leaving the top of the first distillation column to −20° to +50° C., the condensate obtained forming an aqueous phase and an organic phase,
    (c) removing the aqueous phase formed in step (b),
    (d) recycling all or a portion of the organic phase formed in step (b) as a reflux to the top of the first distillation column used in step (a),
    (e) washing the gas not condensed in step (b) containing gaseous vinyl acetate in a washing column with acetic acid containing not more than 10% of water to obtain an acetic acid solution containing vinyl acetate,
    (f) passing a bottom product from step (a) containing vinyl acetate, ethyl acetate, acetic acid and water to a second distillation column and removing a side stream containing ethyl acetate from an enrichment zone above the bottom thereof,
    (g) using all or a portion of the bottom product from step (f) containing acetic acid for the wash in step (e),
    (h) cooling a top vapor from step (f), an aqueous phase and an organic phase being formed,
    (i) removing the aqueous phase formed in step (h),
    (k) recycling a portion of the organic phase formed in step (h) as a reflux to the top of the second distillation column used in step (f),
    (l) passing the remaining portion of the organic phase formed in step (h) together with the acetic acid solution obtained in step (e) and with the remaining portion of the organic phase, formed in step (b), which is not used as a reflux in step (d) into a third distillation column,
    (m) cooling a top vapor from step (1), an aqueous phase and an organic phase being formed,
    (n) removing the aqueous phase formed in step (m),
    (o) recycling the organic phase formed in step (m) as a reflux to the third distillation column used in step (l),
    (p) passing a bottom product from step (l) containing vinyl acetate and acetic acid into a fourth distillation column and
    (q) removing the vinyl acetate at the top of the fourth distillation column used in the (p).

2. A process for isolating vinyl acetate from a gas mixture containing vinyl acetate, ethyl acetate acetic acid, water and carbon dioxide formed in the reaction of ethylene with acetic acid and oxygen in a reaction zone in the gas phase over catalysts containing palladium or palladium compounds, which comprises (a) passing the gas mixture leaving the reaction zone into a first distillation column, (b) cooling the gas mixture leaving the top of the first distillation column to −20° to +50° C., the condensate obtained forming an aqueous phase and an organic phase, (c) removing the aqueous phase formed in step (b), (d) recycling all or a portion of the organic phase formed in step (b) as a reflux to the top of the first distillation column used in step (a), (e) washing the gas not condensed in step (b) containing gaseous vinyl acetate in a washing column with acetic acid containing not more than 10% of water to obtain an acetic acid solution containing vinyl acetate, (f) passing a bottom prodcut from step (a) containing vinyl acetate, ethyl acetate, acetic acid and water to a second distillation column, (g) separating the bottom product from step (f) from ethyl acetate by further distillation and then using all or a portion of this product containing acetic acid for the wash in step (e), (h) cooling a top vapor from step (f), an aqueous phase and an organic phase being formed, (i) removing the aqueous phase formed in step (h), (k) recycling a portion of the organic phase formed in step (h) as a reflux to the top of the second distillation column used in step (f), (l) passing the remaining portion of the organic phase formed in step (h) together with the acetic acid solution obtained in step (e) and with the remaining portion of the organic phase, formed in step (b), which is not used as a reflux in step (d) into a third distillation column, (m) cooling a top vapor from step (1), an aqueous phase and an organic phase being formed, (n) removing the aqueous phase formed in step (m), (o) recycling the organic phase formed in step (m) as a reflux into the third distillation column used in step (l), (p) passing a bottom product from step (1) containing vinyl acetate and acetic acid into a fourth distillation column and (q) removing the vinyl acetate at the top of the fourth distillation column used in step (p).

3. A process for isolating vinyl acetate from a gas mixture containing vinyl acetate, ethyl acetate, acetic acid, water and carbon dioxide formed in the reaction of ethylene with acetic acid and oxygen in a reaction zone in the gas over catalysts containing palladium or palladium compounds, which comprises (a) passing the gas mixture leaving the reaction zone into a first distillation column, (b) cooling the gas mixture leaving the top of the first distillation column to −20° to +50° C., the condensate obtained forming an aqueous phase and an organic phase, (c) removing the aqueous phase formed in step (b), (d) recycling all or a portion of the organic phase formed in step (b) as a reflux to the top of the first distillation column used in step (a), (e) washing the gas not condensed in step (b) containing gaseous vinyl acetate in a washing column with acetic acid containing not more than 10% of water to obtain an acetic acid solution containing vinyl acetate, (f) passing a bottom product from step (a) containing vinyl acetate, ethyl acetate, acetic acid and water to a second distillation column and removing a side stream containing ethyl acetate from an enrichment zone above the bottom thereof, (g) using all or a portion of the bottom product from step (f) containing acetic acid for the wash in step (e), (h) cooling a top vapor of step (f), an aqueous phase and organic phase being formed, (i) removing the aqueous phase formed in step (h), (k) recycling a portion of the organic phase formed in step (h) as a reflux to the top of the second distillation column used in step (f), (l) passing the remaining portion of the organic phase formed in step (h) together with acetic acid solution obtained in step (e) and with the remaining portion of the organic phase, formed in step (b), which is not used as a reflux in step (d) into a third distillation column which contains an intermediate tray, (m) cooling a top vapor from step (l) and recycling substantially all of the condensate formed as a reflux to the top of the third distillation column used in step (l), the remaining portion being discharged for removal of low-boiling constituents, and then removing, from the intermediate tray of the column, the entire reflux and allowing it to separate into an aqueous phase and an organic phase, (n) removing the aqueous phase formed in step (m), (l) recycling the organic phase formed in step (m) to the third distillation column used in step (1), below the intermediate tray, (p) passing a bottom product from step (l) containing vinyl acetate and acetic acid into a fourth distillation column and (q) removing the vinyl acetate at the top of the fourth distillation column used in step (p).

4. The process as claimed in claim 1, wherein the bottom product of step (a) contains 20 to 50% by weight of vinyl acetate.

5. The process as claimed in claim 2, wherein the bottom product of step (a) contains 20 to 50% by weight of vinyl acetate.

6. The process as claimed in claim 3, wherein the bottom product of step (a) contains 20 to 50% by weight of vinyl acetate.

* * * * *

UNITED STATES PATENT AND TRADEMARK OFFICE
CERTIFICATE OF CORRECTION

PATENT NO.  :  4,818,347
DATED       :  April 4, 1989
INVENTOR(S) :  Roscher et al.

It is certified that error appears in the above-identified patent and that said Letters Patent is hereby corrected as shown below:

Column 10, line 55, "(1)," should be --(1),--;

line 65, "the" should be --step--;

line 67, after "acetate" add --,--;

Column 11, line 20, "prodcut" should be --product--;

line 39, "(1)," should be --(1),--;

line 55, after "gas" add --phase--;

Column 12, lines 36 and 37, after "in step" the "(1), the . . ." should follow without a new paragraph;

line 43, "(1)" should be --(o)--;

line 44, "(1)," should be --(1),--.

Signed and Sealed this

Twenty-fourth Day of April, 1990

Attest:

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,818,347

DATED : April 4, 1989

INVENTOR(S) : Roscher et al

It is certified that error appears in the above-identified patent and that said Letters Patent is hereby corrected as shown below:

Column 11, line 45, "(1)" should be --(1),--.

Signed and Sealed this

Tenth Day of July, 1990

*Attest:*

HARRY F. MANBECK, JR.

*Attesting Officer*     Commissioner of Patents and Trademarks